US012697454B2

(12) United States Patent　(10) Patent No.: US 12,697,454 B2
Spayne et al.　(45) Date of Patent: Aug. 4, 2026

(54) SEALING MEMBERS

(71) Applicant: INTERSURGICAL AG, Vaduz (LI)

(72) Inventors: Martin David Spayne, Berkshire (GB); Derek Anthony Mclaughlin, Berkshire (GB); Simon Robert Payne, Berkshire (GB); Matthew James William Leary, Berkshire (GB); Mark Jennings, Berkshire (GB)

(73) Assignee: INTERSURGICAL AG, Vaduz (LI)

( * ) Notice: Subject to any disclaimer, the term of this patent is extended or adjusted under 35 U.S.C. 154(b) by 722 days.

(21) Appl. No.: 18/021,968

(22) PCT Filed: Aug. 19, 2021

(86) PCT No.: PCT/EP2021/073088
§ 371 (c)(1),
(2) Date: Feb. 17, 2023

(87) PCT Pub. No.: WO2022/038245
PCT Pub. Date: Feb. 24, 2022

(65) Prior Publication Data
US 2023/0347088 A1　Nov. 2, 2023

(30) Foreign Application Priority Data
Aug. 21, 2020　(GB) ...................................... 2013108

(51) Int. Cl.
*A61M 16/06*　(2006.01)
*B29C 44/04*　(2006.01)
(Continued)

(52) U.S. Cl.
CPC ..... *A61M 16/0622* (2014.02); *B29C 44/0461* (2013.01); *B29C 45/1676* (2013.01);
(Continued)

(58) Field of Classification Search
CPC .......... A61M 16/0434; A61M 16/0445; A61M 16/0447; A61M 16/06; A61M 16/0616;
(Continued)

(56) References Cited

U.S. PATENT DOCUMENTS 4,454,881 A　6/1984　Huber et al.
10,646,676 B1 *　5/2020　Matich .................... A61L 31/12
(Continued)

FOREIGN PATENT DOCUMENTS

CN　211132535 U　7/2020
JP　2004160783 A　6/2004
(Continued)

OTHER PUBLICATIONS

Hansen, M., "Gas-Assist Injection Molding: An Innovative Medical Technology," Medical Device & Diagnostic Industry pp. 1-6 (2005).
(Continued)

*Primary Examiner* — Joseph D. Boecker
(74) *Attorney, Agent, or Firm* — Troutman Pepper Locke LLP (Rochester)

(57) ABSTRACT

There is provided a method of manufacturing a sealing member (42). The method comprises the steps of: (a) providing a mould having a cavity, a polymer injection port and a gas inlet port (38); (b) injecting a polymer and a blowing agent through the polymer injection port (28) into the cavity of the mould; and (c) introducing gas through the gas inlet port (38) into the cavity of the mould, to form a sealing member (42). The sealing member (42) comprises an internal chamber (44) at least partially bounded by a resiliently deformable enclosing wall formed of the polymer, the enclosing wall including an external surface, the external surface having a form that is determined by the cavity of the mould.

22 Claims, 4 Drawing Sheets

(51) Int. Cl.
*B29C 45/16* (2006.01)
*B29C 45/17* (2006.01)
*B29L 31/48* (2006.01)
(52) U.S. Cl.
CPC ..... *B29C 45/1704* (2013.01); *A61M 2207/00* (2013.01); *B29L 2031/4835* (2013.01)
(58) Field of Classification Search
CPC .......... A61M 16/0622; A61M 2207/00; A61M 2207/10; A41D 13/1146; B29C 44/0461; B29C 45/0013; B29C 45/164; B29C 45/1676; B29C 45/1704; B29C 45/7207; A62B 18/025; B29K 2105/048
See application file for complete search history.

(56) References Cited

U.S. PATENT DOCUMENTS

| | | | | |
|---|---|---|---|---|
| 2006/0185675 A1* | 8/2006 | Colin | .................... | A61M 16/06 |
| | | | | 128/206.28 |
| 2007/0107733 A1* | 5/2007 | Ho | .................... | A61M 16/0622 |
| | | | | 128/206.24 |
| 2010/0024811 A1* | 2/2010 | Henry | ............... | A61M 16/0622 |
| | | | | 128/202.16 |
| 2011/0088699 A1* | 4/2011 | Skipper | ................. | A61M 16/06 |
| | | | | 128/206.26 |

| | | | | |
|---|---|---|---|---|
| 2011/0162650 A1 | 7/2011 | Miller et al. | | |
| 2012/0055485 A1* | 3/2012 | Anthony | ............ | A61M 16/0611 |
| | | | | 128/207.18 |
| 2014/0077406 A1 | 3/2014 | Okamoto et al. | | |
| 2014/0230821 A1* | 8/2014 | Warters | ................. | A61M 16/06 |
| | | | | 128/206.28 |
| 2015/0335845 A1* | 11/2015 | Baiko | ............... | A61M 16/0622 |
| | | | | 128/206.24 |
| 2017/0239437 A1* | 8/2017 | Scheirlinck | ....... | A61M 16/0627 |
| 2019/0307980 A1* | 10/2019 | Haibach | ............ | A61M 16/0605 |
| 2020/0261680 A1* | 8/2020 | Ho | .................... | A61M 16/0622 |
| 2020/0276364 A1* | 9/2020 | Gandola | ................. | C08J 9/142 |

FOREIGN PATENT DOCUMENTS

| | | | | |
|---|---|---|---|---|
| WO | 9921602 A1 | 5/1999 | | |
| WO | WO-03016018 A1 * | 2/2003 | ........ | B29C 45/1704 |
| WO | 2021037768 A1 | 3/2021 | | |

OTHER PUBLICATIONS

International Search Report and Written Opinion for International Application No. PCT/EP2021/073088 (mailed Jun. 12, 2021).
Search Report under Section 17 for GB 2013108.2 (dated Feb. 5, 2021).

* cited by examiner

SEALING MEMBERS

This application is a national stage application under 35 U.S.C. § 371 of International Application No. PCT/EP2021/073088, filed Aug. 19, 2021, which claims the priority benefit of GB Patent Application No. 2013108.2, filed Aug. 21, 2020.

The present invention relates to sealing members, and in particular sealing members for respiratory interface devices, and associated methods of manufacture.

Respiratory apparatus generally includes some form of respiratory interface device in order to connect the respiratory apparatus to the respiratory system of a patient. There are a wide range of different interface devices, including non-invasive interface devices, such as face masks, nasal masks and tracheostomy masks, and also invasive interface devices, such as endotracheal tubes and supraglottic airways, such as laryngeal mask airways.

Many of these interface devices are adapted to seal against a surface of the patient's body, which may be an external or internal surface, in order to form an effective seal with an airway of the patient. For example, non-invasive interface devices typically include a sealing member that seals the device to the face of the patient, thereby forming an effective connection between the device and the mouth and/or nose of the patient, and invasive interface devices often include a sealing member that seals the device to an interior surface of an airway of the patient, thereby forming an effective connection between the device and that airway.

Many of these respiratory interface devices include an inflatable sealing member, eg a sealing cushion or cuff, which is formed by a thin enclosing wall surrounding a gas-charged internal chamber.

One example of a respiratory interface device is an anaesthesia mask. Anaesthesia masks are respiratory masks that are held over the nose and mouth of a patient whilst delivering anaesthesia gases to a patient. These masks typically comprise a mask body, including a tubular connector for connection to a supply of anaesthesia gases, and an inflatable sealing cushion that extends around a peripheral edge of the entrance to the mask body. The wall of the inflatable sealing cushion is thin and requires a sufficient pressure of gas in the interior of the sealing cushion, in excess of atmospheric pressure, to retain its shape and to be resiliently deformable. The sealing cushion typically includes an inlet with a one-way valve, which enables inflation of the sealing cushion. The sealing cushion may also be deflated, using a syringe. In use, a conventional anaesthesia mask with an inflated sealing cushion is placed over the nose and mouth of a patient and urged against the face of the patient until a sufficient seal is achieved that enables anaesthesia gases to be delivered to the patient. However, a significant amount of pressure may need to be applied to achieve an acceptable seal.

A further significant disadvantage with respiratory interface devices including inflatable portions is the cost of manufacture, which typically requires assembly steps of attaching the inflatable portion to the remainder of the device, and in many devices the additional step of providing a valve to enable inflation of the inflatable portion. In particular, blow moulding is commonly used to form an inflatable sealing member and then the inflatable sealing member is glued to a body portion, eg a more rigid mask body. Blow moulding uses either a pre-moulded insert, with a hollow interior, that is inflated within a mould in a process called injection blow moulding, or an extruded parison tube that is clamped at each end and inflated within a mould in a process called extrusion blow moulding.

An alternative approach to the use of an inflatable portion in a respiratory interface device is to provide a sealing member that is anatomically shaped and compliant to provide an effective seal with the patient, eg the patient's face. These devices may be formed in two-shot injection moulding processes that reduce the assembly steps relative to the manufacture of respiratory interface devices having inflatable portions. These masks typically require less pressure to be applied to achieve an acceptable seal. However, these devices suffer from the disadvantage that in the event that an acceptable seal is not achieved, the sealing cushion or cuff is less able to adapt to the patient's face through the application of increased pressure, and there is a risk that if pressure is applied then the seal member will deform and splay, creating a leak.

There has now been devised an improved method of manufacturing a sealing member, and an improved sealing member, which overcome or substantially mitigate the abovementioned and/or other disadvantages associated with the prior art.

The invention has been developed for a specific use in manufacturing sealing members for a respiratory interface device, however it is recognised that the invention may be more widely applicable to uses in other technical fields.

According to a first aspect of the invention, there is provided a method of manufacturing a sealing member, the method comprising the steps of:

(a) providing a mould having a cavity, a polymer injection port and a gas inlet port;

(b) injecting a polymer and a blowing agent through the polymer injection port into the cavity of the mould; and (c) introducing gas through the gas inlet port into the cavity of the mould, to form a sealing member, wherein the sealing member comprises an internal chamber at least partially bounded by a resiliently deformable enclosing wall formed of the polymer, the enclosing wall including an external surface, the external surface having a form that is determined by the cavity of the mould.

The method of manufacture according to the invention has been found to be advantageous in that when it is used to manufacture a sealing member for a respiratory interface device, the external surface of the resiliently deformable enclosing wall can be shaped to provide an anatomical fit with a patient's face, which provides the sealing member with an effective seal with a patient by virtue of its anatomical fit, whilst the internal chamber bounded by the enclosing wall also enables the sealing member to be urged against the patient, eg against the patient's face, in the event that the seal needs to be improved. In particular, where gas is allowed to exit the internal chamber, in use, this increases the deformability of the sealing member for a given thickness of the resiliently deformable enclosing wall. This enables a thicker wall thickness than in the inflatable sealing members of the prior art that do not allow gas to exit the internal chamber during use, and this thicker wall thickness may provide advantages including enabling the anatomical shape to be better retained during and after deformation, enabling improved durability and reduced risk of damage, and enabling a sealing member that does not need to be re-inflated before use. Furthermore, relative to sealing members of the prior art that are not inflatable, the arrangement of this aspect of the invention reduces the risk that the sealing member will splay, creating a leak, when pressure is applied by a clinician.

When manufacturing sealing members using gas-assisted injection moulding, it was found that it was advantageous to inject at least a minimum volume of polymer to prevent the injected gas from blowing through the exterior surface of the polymer upon gas injection, which would create a hole (or at least a deformed or weakened portion) in the external surface of the resultant sealing member. Furthermore, the injection of a greater volume of the polymer was also found to result in a more uniform enclosing wall and internal chamber in the resultant sealing member.

However, it was found that the volume of polymer required to provide these advantages may result in an enclosing wall having a greater thickness than desired, which increased the resilience of the external surface of the sealing member, and when used in respiratory interface devices, may make it more difficult to urge against a patient's face to create a seal, meaning a softer material may have to be used to form the sealing member, which would be undesirable.

It was found that the introduction of a blowing agent, mixed with the polymer, and the expansion of the blowing agent in the cavity of the mould, may increase the volume of the cavity that is taken up by the polymer body after injection into the cavity of the mould, without increasing the thickness of the enclosing wall in the resultant sealing member. In particular, because the blowing agent expands within the polymer, the volume of the mix of the polymer and the blowing agent may be greater than the volume of the polymer if it were to be injected alone. The surface area of the polymer may also be increased relative to a polymer injected without a blowing agent. This may allow less polymer to be injected and a reduced enclosing wall thickness in the resultant sealing member, whilst still achieving the minimum volume of polymer body required in the cavity to prevent blow-through when the gas is introduced and provide a more uniform enclosing wall and internal chamber in the resultant sealing member.

Without wishing to be bound by theory, it is thought that the increased volume of the cavity that is taken up by the polymer body may cause the polymer body to contact the walls of the cavity. Since the walls of the cavity are the coolest part of the cavity, the polymer and blowing agent mix that is in contact with the walls may cool first, and a solidified (or at least more viscous) skin layer may be formed at the walls of the cavity. It is thought that this may lead to a hardened or more viscous skin layer at the walls of the cavity, which may encompass a less viscous core of the polymer body that extends along a central longitudinal axis of the cavity of the mould. This skin layer and less viscous core is thought to create a path of least resistance for the gas—along a central longitudinal axis of the cavity of the mould. It is thought that, when introduced, the gas may push the core of the polymer body, or a substantial part thereof, through the cavity, with the skin layer remaining at the walls of the cavity, thereby forming an internal chamber that is at least partially bounded by an enclosing wall of polymer.

It is thought that the creation of a path of least resistance along the central longitudinal axis of the cavity of the mould may be enhanced by the formation of gas pockets resulting from the blowing agent. Whilst the polymer and blowing agent mix retains sufficient heat, the blowing agent may expand to form gas pockets in the polymer and blowing agent mix within the cavity. Since the walls of the cavity are the coolest part of the cavity, the polymer and blowing agent mix in contact with the walls may cool first and thus expansion of the blowing agent at the walls of the cavity may slow and/or stop first. This may lead to a difference in the size of gas pockets formed in the polymer and blowing agent mix within the cavity, the size of the gas pockets increasing with distance from the walls of the cavity. This difference in size is thought to enhance the creation of a path of least resistance along a central longitudinal axis of the cavity of the mould.

Hence, the addition of a blowing agent may enable greater control and predictability over the final form of the sealing member, without increasing the thickness of the enclosing wall, for example.

The blowing agent may be a substance that, when mixed with the polymer, expands to produce gas pockets within the polymer, for example via a foaming process, and the polymer undergoes a period of hardening, or a phase transition, following formation of the gas pockets. The blowing agent may therefore cause the polymer to adopt a cellular structure.

The shape of the external surface may be determined by the cavity of the mould. The dimensions of the external surface may be determined by the mould, such as the radius and/or the diameter of the external surface. The volume of the sealing member may be determined by the cavity of the mould. The final form of the material formed from the polymer and the blowing agent may be determined by the cavity of the mould. The shape and/or dimensions of the external surface may match, or correspond to, the shape and/or dimensions of the cavity of the mould. The volume of the sealing member may match, or correspond to, the volume of the cavity of the mould.

The injection of gas through the gas inlet port into the cavity of the mould may be maintained until the sealing member adopts its final form. However, the pressure of the injected gas may change after formation of the internal chamber. For example, the pressure may be reduced, provided there is enough pressure to prevent the sealing member from separating from the walls of the cavity and collapsing inwardly into the cavity of the mould. Once the blowing agent has completed its expansion in the polymer-blowing agent mix, the continued injection of gas may cause the volume of the mix of the polymer and the blowing agent to be reduced.

The blowing agent may expand in the cavity of the mould, rather than after the mould has been opened. This feature may facilitate formation of a skin layer at the walls of the cavity, which may enable an external surface of the sealing member to have a predetermined form, such as an anatomically shaped sealing member for a respiratory interface device, and the subsequent introduction of gas to form an internal chamber.

Hence, according to a further aspect of the invention, there is provided a method of manufacturing a sealing member, the method comprising the steps of: (a) providing a mould having a cavity, a polymer injection port and a gas inlet port; (b) injecting a polymer and a blowing agent through the polymer injection port into the cavity of the mould; and (c) introducing gas through the gas inlet port into the cavity of the mould, to form a sealing member; wherein the blowing agent expands in the cavity of the mould, and wherein the sealing member comprises an internal chamber at least partially bounded by a resiliently deformable enclosing wall formed of the polymer, the enclosing wall including an external surface.

The sealing member may adopt its final form in the cavity of the mould. A small amount of expansion occurring outside of the cavity of the mould may be unavoidable. However, the blowing agent may expand by less than 10%, less than 5%, or less than 1% of its total expansion once removed from the cavity. The sealing member may cool in the cavity of the mould, eg to a temperature that is low enough for the sealing member to undergo no substantial change of inherent shape or dimensions upon removal from the cavity of the mould. A small amount of change in the inherent shape or dimensions upon removal from the cavity of the mould may be unavoidable. For example, the dimensions of the sealing member may decrease slightly due to further cooling upon removal from the cavity of the mould. The sealing member may fully set or fully solidify in the cavity of the mould.

The internal chamber at least partially bounded by a resiliently deformable enclosing wall formed of the polymer may be formed in the sealing member in the cavity of the mould. This feature may facilitate formation of an external surface having a predetermined form, such as an anatomically shaped sealing member for a respiratory interface device.

Hence, according to a further aspect of the invention, there is provided a method of manufacturing a sealing member, the method comprising the steps of: (a) providing a mould having a cavity, a polymer injection port and a gas inlet port; (b) injecting a polymer and a blowing agent through the polymer injection port into the cavity of the mould; and (c) introducing gas through the gas inlet port into the cavity of the mould to form a sealing member, such that an internal chamber at least partially bounded by a resiliently deformable enclosing wall formed of the polymer is formed in the sealing member in the cavity of the mould, the enclosing wall including an external surface.

The internal chamber may be formed in the sealing member before the sealing member is removed from the cavity of the mould. The cavity of the mould may be formed of at least two portions that are brought into engagement to define the cavity. The internal chamber may be formed whilst the at least two portions remain in engagement. The internal chamber may be formed before the at least two portions are disengaged.

The internal chamber may be charged with gas during manufacture, which may be replaced with ambient air once the sealing member has been removed from the mould. The sealing member may include an opening, or a fluid passageway, that enables gases or ambient air to enter, or exit, the internal chamber.

Each of the blowing agent, the polymer and the gas may be injected or introduced into the same cavity of the same mould. The blowing agent may be mixed with the polymer prior to injection through the polymer injection port into the cavity of the mould, and the gas may be first introduced through the gas inlet port into the cavity of the mould after the cavity of the mould is at least partially charged by the mixed polymer and blowing agent. This feature may facilitate formation of a uniform internal chamber.

Hence, according to a further aspect of the invention, there is provided a method of manufacturing a sealing member, the method comprising the steps of: (a) providing a mould having a cavity, a polymer injection port and a gas inlet port; (b) mixing a blowing agent with a polymer; (c) injecting the mixed polymer and blowing agent through the polymer injection port into the cavity of the mould; and (d) first introducing gas through the gas inlet port into the cavity of the mould after the cavity of the mould is at least partially charged by the mixed polymer and blowing agent, to form a sealing member, wherein the sealing member comprises an internal chamber at least partially bounded by a resiliently deformable enclosing wall formed of the polymer, the enclosing wall including an external surface.

During mixing of the blowing agent with the polymer, the blowing agent may be uniformly distributed throughout the polymer, for example using a volumetric dosing unit. This ensures that the blowing agent expands uniformly and predictably throughout the cavity of the mould.

At completion of the step of injection of the mixed polymer and blowing agent through the polymer injection port into the cavity of the mould, the cavity of the mould may be only partially charged. Therefore, upon completion of charging, the cavity of the mould is only partially charged. The volume of the mixed polymer and blowing agent that is injected into the cavity of the mould may therefore be less than the volume of the cavity of the mould.

Preferably, injection of the mixed polymer and blowing agent through the polymer injection port into the cavity of the mould commences before the introduction of gas through the gas inlet port into the cavity of the mould. The introduction of gas through the gas inlet port into the cavity of the mould may commence after completion of the partial charging of the cavity of the mould, ie after the total volume of mixed polymer and blowing agent is injected through the polymer injection port into the cavity of the mould. There may be a time delay between completion of the partial charging of the cavity of the mould and the introduction of gas through the gas inlet port into the cavity of the mould.

The mixed polymer and blowing agent is herein referred to as a mix, for ease. During injection of the mix, the mix will be soft enough to flow, eg in the form of a melt. Following injection of the mix, but prior to introduction of gas, the mix may extend only partially along the cavity. The mix may at this time have the form of a unitary body, which is separated from the end of the cavity opposite to the end of the cavity at which the polymer injection port is disposed.

The polymer injection port for the cavity may be disposed at one end of the sealing member during manufacture, and the sealing member may be formed by the mix flowing in both directions, from the polymer injection port, along the cavity.

The injected gas may guide, deform and/or move the mix, within the cavity of the mould, to form the sealing member. The gas may apply pressure to the mix to form the internal chamber and the enclosing wall of the polymer. The pressure applied by the gas may have a radial component, which may guide, deform or move the mix outwardly, towards the interior surfaces of the cavity, and may thereby form the enclosing wall of the sealing member. The pressure applied by the gas may have an axial component, which may guide, deform or move the mix axially, along the cavity away from the gas inlet port.

The step of introducing gas into the cavity of the mould, through the gas inlet port, may form a bubble of gas within the mix, extending from the gas inlet port. The gas inlet port may be disposed at one end of the sealing member during manufacture, and the internal chamber may be formed by the injected gas flowing in both directions, from the gas inlet port, through the mix, along the cavity.

However, other arrangements may be used, including multiple gas inlet ports in different regions of the cavity.

The gas that is introduced into the cavity may also move the mix along the cavity, for example towards the end of the cavity opposite to the end of the cavity at which the polymer injection port and/or the gas inlet port is disposed.

The mix may be moved along the cavity in opposite directions from the polymer injection port and/or the gas inlet port, where the cavity has the form of a closed loop, such that the mix has two branches that advance along the cavity. The branches of the mix may meet, and may join and bond, thereby forming a sealing member of the respiratory interface device that extends along a closed loop.

One or more additional gas inlet ports may be provided in order to enable introduction of a gas with a pressure that counterbalances the movement of the polymer along the cavity. As the polymer moves along the cavity, the gas introduced through the one or more additional gas inlet ports may be vented.

The polymer and the blowing agent may be injected through the polymer injection port into the cavity of the mould such that the cavity of the mould is only partially charged. This feature may facilitate formation of an internal chamber to be formed by the introduction of gas.

Hence, according to a further aspect of the invention, there is provided a method of manufacturing a sealing member, the method comprising the steps of: (a) providing a mould having a cavity, a polymer injection port and a gas inlet port; (b) injecting a polymer and a blowing agent through the polymer injection port into the cavity of the mould such that the cavity of the mould is only partially charged; and (c) introducing gas through the gas inlet port into the cavity of the mould, to form a sealing member, wherein the sealing member comprises an internal chamber at least partially bounded by a resiliently deformable enclosing wall formed of the polymer, the enclosing wall including an external surface.

The polymer and blowing agent that are injected into the cavity of the mould may have a combined volume that is less than the volume of the cavity. Injection of the polymer and the blowing agent through the polymer injection port into the cavity of the mould may stop once the cavity is partially filled, eg to a predetermined level.

The blowing agent may be a physical blowing agent. It is believed that the provision of a physical blowing agent is advantageous because, at a given temperature and pressure, a physical blowing agent has a limit to its expansion, which enables a greater predictability of the physical blowing agent's behaviour, and hence a greater control over the expansion of the blowing agent and the resultant sealing member.

Hence, according to a further aspect of the invention, there is provided a method of manufacturing a sealing member, the method comprising the steps of: (a) providing a mould having a cavity, a polymer injection port and a gas inlet port; (b) injecting a polymer and a blowing agent through the polymer injection port into the cavity of the mould; and (c) introducing gas through the gas inlet port into the cavity of the mould, to form a sealing member, wherein the sealing member comprises an internal chamber at least partially bounded by a resiliently deformable enclosing wall formed of the polymer, the enclosing wall including an external surface, wherein the blowing agent is a physical blowing agent.

The physical blowing agent may be caused to expand by one of, or a combination of, the application of heat and a reduction in pressure on injection of the polymer and blowing agent mix into the cavity of the mould. The polymer and physical blowing agent mix may be heated before injection into the cavity of the mould and/or the cavity of the mould may be heated. The reduction in pressure may be achieved by the cavity of the mould only being partially charged by the polymer and physical blowing agent mix in the injection moulding step.

Where gas is produced by the physical blowing agent, it may be by a physical process, eg by a phase change, such as the vaporisation of a liquid. The production of gas by the physical blowing agent may involve no chemical reactions.

In contrast, the production of gas in a chemical blowing agent is by means of a chemical reaction. The gas produced by the physical blowing agent may expand, and hence its volume increase, by a physical process, eg by an increase in temperature and/or a reduction in pressure.

It is believed that a physical blowing agent that acts in this way is advantageous because it expands under a wider range of conditions, and is therefore more adaptable. For example, although there is an optimum working temperature at which the aforementioned physical blowing agent will expand most efficiently, it is believed that they still expand controllably over a wide temperature range.

The physical blowing agent may have a multi-layered structure. For example, the physical blowing agent may have a core-shell structure. The shell layer may surround or encapsulate the core layer. The core-shell structure may be substantially spherical. The shell may be formed of a solid material, such as a polymer. The polymer may be a thermoplastic, such as an acrylonitrile polymer or a nitrile, eg polyacrylonitrile or acrylonitrile. The core layer may comprise the gas or gas-producing material of the physical blowing agent, which may be a liquid. The gas or liquid may be a hydrocarbon, such as an octane isomer, eg trimethylpentane, or a pentane isomer, eg pentane or isopentane, or any combination thereof. In the trade, blowing agents having this structure may be referred to as microspheres. The core layer may produce gas and/or expand within the shell layer in response to the application of heat from a source external of the blowing agent. The polymer (and blowing agent) may heat to a temperature of 50-300 degrees Celsius, 75-250 degrees Celsius, or 80-235 degrees Celsius. The volume of the core layer and/or the microsphere may increase in response to the application of heat and/or a reduction in pressure from a source external of the blowing agent. The diameter of the core layer and/or the microsphere may increase in response to the application of heat and/or a reduction in pressure from a source external of the blowing agent. The thickness of the shell layer may decrease in response to the application of heat and/or a reduction in pressure from a source external of the blowing agent. In a particularly preferred embodiment, the physical blowing agent may be a liquid that can be vaporised to produce gas, the liquid being surrounded or encapsulated by a solid shell layer.

Prior to the expansion within the polymer, the diameter of the microsphere may be in the range of 5-20 $\mu$m, 8-15 $\mu$m, or 10-12 $\mu$m. Following expansion within the polymer, the diameter of the microsphere may be in the range of 10-1000 $\mu$m, 25-750 $\mu$m, or 50-500 $\mu$m, 10-200 $\mu$m, 20-160 $\mu$m, or 30-140 $\mu$m.

Prior to the expansion within the polymer, the thickness of the shell layer may be in the range of 1-2.5 $\mu$m, 1.25-2.25 $\mu$m, or 1.5-2 $\mu$m. Following expansion within the polymer, the thickness of the shell layer may be in the range of 0.01-0.25 $\mu$m, 0.05-0.2 $\mu$m, or 0.1-0.15 $\mu$m. Following expansion within the polymer, the thickness of the shell layer may decrease to 1-20%, 2.5-15%, or 5-10% of the thickness of the shell layer prior to the expansion within the polymer.

The gas inlet port of the mould may be connected to a source of gas, which may include a controller for determining the volume, pressure, temperature and/or time period for the introduction of gas. The gas may have a pressure that is sufficient to guide, deform and/or move the polymer to form the sealing member within the cavity of the mould. For example, the gas may be injected, eg through a gas injection port, and may be supplied from a compressed source. Where gas is provided by a compressed source, the gas may be nitrogen, or another sufficiently inert gas.

The gas inlet port for the cavity may be disposed adjacent to the polymer injection port for the cavity. The gas inlet port of the mould may project into the cavity, eg in the form of a nozzle. The gas inlet port may project relative to a surrounding interior surface of the mould that defines the cavity. The gas inlet port may have an exit opening into the cavity through which the gas enters the cavity.

The exit opening of the gas inlet port may be formed in a wall of the mould. The exit opening may be separated from a surrounding interior surface of the mould that defines the cavity. The exit opening may be substantially centrally positioned relative to a transverse cross-section of the cavity, eg disposed in the range of 35-65% of the longest dimension of the transverse cross-section of the cavity. By transverse plane is meant a plane of the cavity that is orientated substantially perpendicularly to a central axis of the cavity, which extends along the centre of the cavity in a loop.

The gas inlet port may project relative to a surrounding interior surface of the mould that defines the cavity, which may cause an aperture to be formed in the enclosing wall of the sealing member. The aperture may be in fluid communication with the internal chamber of the sealing member. In some embodiments, after completion of the step of introducing gas through the gas inlet port into the cavity of the mould and a step of removing the gas inlet port from the mould, the aperture may be sealed or filled. The aperture may be sealed or filled by injecting polymer through the polymer injection port into the cavity of the mould. Alternatively, the aperture may be sealed or filled by inserting a plug, or by any other conventional means.

The sealing member defined in any of the methods defined above may be for a respiratory interface device, and the external surface defined in any of the methods above may be a patient-contacting surface.

The patient contacting-surface may provide an anatomical fit with a patient. As discussed above, the method of manufacture according to the invention may be advantageous in that when it is used to manufacture a sealing member for a respiratory interface device, the external surface of the resiliently deformable enclosing wall can be shaped to provide an anatomical fit with a patient's face, which provides the sealing member with an effective seal with a patient by virtue of its anatomical fit, whilst the internal chamber bounded by the enclosing wall also enables the sealing member to be urged against the patient, eg against the patient's face, in the event that the seal needs to be improved.

Hence, according to a further aspect of the invention, there is provided a method of manufacturing a sealing member for a respiratory interface device, the method comprising the steps of: (a) providing a mould having a cavity, a polymer injection port and a gas inlet port; (b) injecting a polymer and a blowing agent through the polymer injection port into the cavity of the mould; and (c) introducing gas through the gas inlet port into the cavity of the mould, to form a sealing member for a respiratory interface device, wherein the sealing member comprises an internal chamber at least partially bounded by a resiliently deformable enclosing wall formed of the polymer, the enclosing wall including a patient-contacting surface, the patient-contacting surface providing an anatomical fit with a patient.

According to a further aspect of the invention, there is provided a sealing member manufactured by any of the methods defined above. According to a further aspect of the invention, there is provided a respiratory interface device comprising a sealing member manufactured by any of the methods defined above.

According to a further aspect of the invention, there is provided a sealing member for a respiratory interface device, the sealing member comprising an internal chamber at least partially bounded by a resiliently deformable enclosing wall, the enclosing wall including a patient-contacting surface, the enclosing wall having a plurality of gas pockets formed therein and the patient-contacting surface providing an anatomical fit with a patient.

The gas in the gas pockets may be gas produced by the use of a blowing agent during manufacture of the sealing member, for example by the methods of manufacture according to the invention, or may be ambient air that has filled the pockets after manufacture of the sealing member. The gas pockets may be akin to bubbles, a cellular structure, or a matrix of holes in their appearance.

The majority of gas pockets formed in the enclosing wall may have a diameter in the range of 10-1000 μm, 25-750 μm, or 50-500 μm, 10-200 μm, 20-160 μm, or 40-120 μm.

It is thought that the average size of the gas pockets formed at or towards the external surface, ie the patient-contacting surface, of the enclosing wall, may be less than the average size of the majority of gas pockets formed at an internal surface of the enclosing wall, ie the surface of the enclosing wall that at least partially bounds the internal chamber. It is thought that the average size of the gas pockets may increase across the thickness of the enclosing wall, ie from the external surface of the enclosing wall to the inner surface of the enclosing wall. The average size may refer to the average diameter and/or the average surface area and/or the average volume of the gas pockets, and the average may refer to the mean value, the median value or the mode value.

The majority of gas pockets formed at or towards the external surface of the enclosing wall, ie at or towards the patient-contact surface, may have a diameter in the range of 10-90 μm, 25-80 μm, or 40-70 μm. At least some of the gas pockets formed at or towards the inner surface of the enclosing wall may have a diameter in the range of 200-1000 μm, 250-750 μm, or 350-500 μm.

The average density of the gas pockets formed in the enclosing wall throughout the majority of the enclosing wall may be in the range of 1-500,000 gas pockets per mm3, 50-125,000 gas pockets per mm3, or 5,000-50,000 gas pockets per 25 mm3.

In order to provide an anatomical fit, the patient-contacting surface may have a leading portion, ie a portion that contacts a surface of the patient before any deformation of the sealing member, that is anatomically shaped. The anatomical shape may be determined at least in the direction of engagement of the sealing member with a surface of the patient, such that the position of the leading portion of the patient-contacting surface varies in this direction, eg at different positions along the patient-contacting surface. The leading portion of the patient-contacting surface may have the form of a closed loop, for example extending around a mask body for a respiratory mask, or an airway tube for a laryngeal mask airway or an endotracheal tube. The leading portion and/or a central line on the leading portion of the patient-contacting surface may have a varying position relative to a reference surface, such as a reference plane or a reference cylindrical surface, where the reference surface may be arranged perpendicularly to the direction of engagement of the sealing member with the surface of the patient, or the direction of global pressure applied by the sealing member to the surface of the patient. The leading portion and/or a central line on the leading portion of the patient-contacting surface may have a position relative to a reference surface that varies non-linearly.

The patient-contacting surface of the sealing member may therefore be formed with a pre-determined anatomical shape. The patient-contacting surface of the sealing member may have the form of a closed loop.

Where the sealing member is for a respiratory mask, the patient-contacting surface may be generally aligned with the frontal plane of a patient, in use, but may comprise convex surfaces at cheek regions of the patient-contacting surface, and/or concave surfaces at nose and/or chin regions of the patient-contacting surface, in a circumferential direction. The patient-contacting surface may comprise convex surfaces in a transverse, or radial, direction. The circumferential convex surfaces of the patient-contacting surface may extend along the majority of the length of the mask, and/or the circumferential concave surfaces of the patient-contacting surface may extend along the width of the mask, eg at each end. The convex and/or concave curvature may provide a patient-contacting surface with a varying position relative the sagittal axis of the patient, in use.

Where the sealing member is for a laryngeal mask airway or an endotracheal tube, the sealing member may have a shape that provides an anatomical fit with a patient's larynx or trachea.

The longitudinal axis of the sealing member may correspond to the longitudinal axis of the patient, when the sealing member is fitted to a patient. For a sealing member for a respiratory mask, the gas inlet port may be disposed at the end of the cavity that corresponds to the apex of the nose portion of the sealing member for a respiratory mask.

In a respiratory mask, the aperture in the sealing member may provide fluid communication between the internal chamber of the sealing member and ambient air. In an invasive respiratory interface device, such as a laryngeal mask airway, the aperture in the sealing member may provide fluid communication between the internal chamber of the sealing member and a source of gas for inflating the sealing member.

The sealing member may include an aperture in fluid communication with the internal chamber of the sealing member and with ambient air, such that ambient air may enter and exit the internal chamber during use. Where multiple internal chambers are provided, each internal chamber may be provided with an aperture in the enclosing wall of the sealing member. The aperture, or apertures, may be provided in the enclosing wall of the sealing member.

In a respiratory mask, the aperture in the sealing member may provide fluid communication between the internal chamber of the sealing member and ambient air. In this embodiment, if the seal needs to be improved, in use, the user may urge the sealing member against the patient's face, eg by applying pressure on the respiratory device interface towards the patient's face. The sealing member and the internal chamber would be compressed, causing air to exit the internal chamber, but the resilience of the sealing member may be sufficient for the internal chamber not to fully collapse, ie there remains a separation between opposing internal surfaces of the enclosing wall, and to return to its original shape once the pressure has been removed.

The aperture may be normally open, or may be opened by the flow of air into and out of the internal chamber of the sealing member. The aperture may be devoid of any valve having a closed configuration. In some embodiments, the aperture may include a valve that regulates the flow of ambient air into and out of the internal chamber of the sealing member.

In an invasive respiratory interface device, such as a laryngeal mask airway, the aperture in the sealing member may provide fluid communication between the internal chamber of the sealing member and a source of gas for inflating the sealing member, and hence may form part of a supply conduit or a connector for a supply conduit.

According to a further aspect of the invention, there is provided a sealing member, the sealing member comprising an internal chamber at least partially bounded by a resiliently deformable enclosing wall, the enclosing wall including an external surface, the enclosing wall having a plurality of gas pockets formed therein, the sealing member having the form of a loop, and the internal chamber of the sealing member being continuous and extending around at least a majority of the loop.

The internal chamber may have a central longitudinal axis that follows a curved path. The curved path may extend around at least the majority of the loop.

The loop may be circular, elliptical, triangular or oblong-like in nature. For example, the sealing member may be a sealing membrane for a respiratory interface device, and the external surface may be a patient-contacting surface.

The patient-contacting surface may have an aperture formed therein for receiving a nasal and/or mouth region of a patient's face. The patient-contacting surface and/or the aperture therein be may substantially triangular in nature, ie to match the shape of the nose and mouth of the patient's face.

The internal chamber may extend around at least 80%, or at least 90%, of the length of the loop. The internal chamber may extend around 80-100%, 80-90%, or 90-100% of the length of the loop. The length of the loop may refer to the length of the central axis of the loop. The loop may extend through an angle of 360 degrees, and the internal chamber may extend through an angle of 300-360 around the loop, through an angle of 300-330 degrees around the loop, or through an angle of 330-360 degrees around the loop. In some examples, the internal chamber may extend around the entirety of the loop, ie the internal chamber may also form a loop.

The internal chamber may be charged with gas during manufacture. The thickness of the enclosing wall that is formed may be less than 6 mm, less than 5 mm, less than 4 mm, less than 3 mm or less than 2.5 mm. The enclosing wall may have a thickness in the range of 0.5-6 mm, 1-4 mm, or 1.5-2.5 mm The enclosing wall may have a substantially uniform thickness, at least over the majority of the internal chamber, eg less than 20% variation from mean thickness over at least 80% of the surface area of the enclosing wall. In certain regions of the enclosing wall, the thickness may be increased to provide an increased resistance to deformation in use, or decreased to provide a decreased resistance to deformation in use.

The internal chamber may have a substantially constant radius and/or diameter throughout the majority of the internal chamber, ie along its length around the loop. The cross-sectional area of the internal chamber may be substantially constant throughout the majority of the internal chamber, ie along its length around the loop. The internal chamber may have a substantially constant cross-sectional area, at least throughout the majority of the internal chamber, eg less than 20% variation from mean cross-sectional area over at least 80% along its length around the loop.

The length of the internal chamber around the loop may be defined as the length of the central longitudinal axis of the internal chamber around the loop of the sealing member.

The external surface may be arranged to substantially retain its shape in the absence of an applied internal pressure. The external surface may have a rigidity and/or thickness that enables it to substantially retain its shape in the absence of an applied internal pressure.

The cross-sectional area of the internal chamber may vary, for example by virtue of variation of the position and/or thickness of the enclosing wall.

The sealing member may have one or more solid portion, ie a portion without an internal chamber. The one or more solid portion may be disposed at the opposite end of the cavity from the gas inlet port. Where the internal chamber extends around less than 100% of the length of the loop, the internal chamber may therefore have a first end and a second end, which may be separated by the one or more solid portion. The one or more solid portion may be a single continuous solid portion. The single continuous solid body may be of the second polymer. The internal chamber may comprise tapered end portions adjacent to the one or more solid portion of the sealing member.

The solid portion may provide the sealing member with greater resistance to deformation in one or more selected regions. For example, the solid portion may provide a sealing member of a respiratory mask with greater resistance to deformation in one or more selected regions, eg in a chin region, which may remove the need for separate reinforcement formations. Similarly, this solid portion may provide a tip region of a sealing cuff of a laryngeal mask airway with greater resistance to deformation, which may reduce the risk of the sealing cuff folding during insertion into a patient's airway, and which may remove the need for separate reinforcement formations.

The solid portion may comprise one or more solid portion. The first and second ends of the internal chamber may be separated by the one or more solid portion.

The method of manufacturing a sealing member of a respiratory interface device according to the invention has also been found to enable manufacture of a respiratory interface device with less assembly steps, reduced time of manufacture and reduced cost of manufacture, relative to prior art methods for manufacturing inflatable sealing members, such as methods that utilise blow moulding. In particular, it has been found that the method of manufacturing a sealing member of a respiratory interface device according to the invention may be incorporated into manufacturing processes in which the step of forming the sealing member also fixes the sealing member to a body portion of the respiratory interface device, such as two-shot moulding or overmoulding processes. This has not conventionally been possible when manufacturing respiratory interface devices having inflatable sealing members.

According to further aspects of the invention, there are provided methods of manufacturing a respiratory interface device. The methods of manufacture may be a two-shot moulding process or an overmoulding process, and in both of these processes the body portion of the respiratory interface device will typically be the earlier-formed portion, and the sealing member of the respiratory interface device will typically be the later-formed portion. These two embodiments are defined separately below.

According to a further aspect of the invention, there is provided a method of manufacturing a respiratory interface device, the method comprising the steps of:

(a) providing a mould having a first-shot configuration defining a first cavity and a first polymer injection port, and a second-shot configuration defining a second cavity, a second polymer injection port and a gas inlet port opening into the second cavity;

(b) arranging the mould in the first-shot configuration;

(c) injecting a first polymer through the first polymer injection port into the first cavity of the mould to form a body portion of the respiratory interface device;

(d) arranging the mould in the second-shot configuration, such that the body portion of the respiratory interface device is disposed adjacent to the second cavity; and (e) injecting a second polymer and a blowing agent through the second polymer injection port into the second cavity of the mould, and introducing gas through the gas inlet port into the second cavity of the one or more moulds, to form a sealing member of the respiratory interface device, the sealing member being brought into engagement with the body portion, during injection moulding of the sealing portion, in a manner that fixes the body portion and the sealing member of the respiratory interface device together, and the sealing member of the respiratory interface device comprising an internal chamber at least partially bounded by a resiliently deformable enclosing wall formed of the second polymer, the enclosing wall including a patient-contacting surface.

According to a further aspect of the invention, there is provided a method of manufacturing a respiratory interface device, the method comprising the steps of:

(a) providing a first mould having a first cavity and a first polymer injection port, and a second mould having a second cavity, a second polymer injection port and a gas inlet port opening into the second cavity;

(b) injecting a first polymer through the first polymer injection port into the first cavity of the first mould to form a body portion of the respiratory interface device;

(c) transferring the body portion of the respiratory interface device to the second mould, such that the body portion of the respiratory interface device is disposed within or adjacent to the second cavity; and (d) injecting a second polymer and a blowing agent through the second polymer injection port into the second cavity of the second mould, and introducing gas through the gas inlet port into the second cavity of the second mould, to form a sealing member of the respiratory interface device, the sealing member being brought into engagement with the body portion, during injection moulding of the sealing portion, in a manner that fixes the body portion and the sealing member of the respiratory interface device together, and the sealing member of the respiratory interface device comprising an internal chamber at least partially bounded by a resiliently deformable enclosing wall formed of the second polymer, the enclosing wall including a patient-contacting surface.

The patient-contacting surface may have a form that is determined by the second cavity of the mould. The patient-contacting surface may provide an anatomical fit with a patient. The blowing agent may expand in the second cavity of the mould. The internal chamber at least partially bounded by a resiliently deformable enclosing wall formed of the polymer may be formed in the sealing member in the second cavity of the mould. The second cavity of the mould may be only partially charged by the second polymer and the blowing agent. The blowing agent may be activated by the application of heat. The polymer may be mixed with the blowing agent prior to injection into the second cavity of the mould, and the gas may be introduced through the gas inlet port into the second cavity of the mould when it is at least partially charged by the mixed polymer and blowing agent. The internal chamber at least partially bounded by a resiliently deformable enclosing wall formed of the polymer may be formed in the sealing member in the second cavity of the mould.

The second cavity of the mould may be only partially charged by the second polymer and the blowing agent. This allows expansion of the sealing member to form an internal chamber to occur whilst the sealing member is in the cavity mould, which enables greater control over the expansion, and hence greater control over the resultant enclosing wall and internal chamber.

The gas inlet port of the mould may project into the second cavity. The gas inlet port may project relative to a surrounding interior surface of the mould that defines the second cavity. Alternatively, the gas inlet port may project through the body portion of the respiratory mask into the second cavity. In a two-shot moulding process, the gas inlet port may project relative to a surrounding interior surface of the mould that defines the first cavity in the first-shot configuration of the mould, such that when the first polymer is injected into the first cavity of the mould to form a body portion of the respiratory interface device, the gas inlet port extends through the first polymer in the first cavity, and the gas inlet port may then project through the body portion of the respiratory mask into the second cavity in the second-shot configuration of the mould.

The gas inlet port may have an exit opening into the second cavity through which the gas enters the second cavity. The exit opening of the gas inlet port may be aligned with a longitudinal axis of the second cavity, and hence a longitudinal axis of the respiratory interface device. The longitudinal axis of the respiratory interface device may correspond to the longitudinal axis of the patient, when the respiratory interface device is fitted to a patient. For a respiratory mask, the gas inlet port may be disposed at the end of the second cavity that corresponds to the apex of the nose portion of the respiratory mask.

An aperture into the internal chamber may be formed around the gas inlet port, during manufacture, which aperture enables ambient air to enter and exit the internal chamber, in use. The aperture may be formed in the resiliently deformable enclosing wall formed of the second polymer. Alternatively, the internal chamber may be at least partially bounded by a wall having a first layer defined by the first polymer and a second layer defined by the second polymer, and the aperture into the internal chamber may formed in said wall.

The gas inlet port may project relative to a surrounding interior surface of the mould that defines either the first or second cavity, which may cause an aperture to be formed in either the body portion of the respiratory device, and/or the enclosing wall of the sealing member of the respiratory interface device. The aperture may be in fluid communication with the internal chamber of the sealing member of the respiratory interface device.

In a respiratory mask, the aperture may therefore be formed in the mask body and/or the sealing member, and the aperture may provide fluid communication between the internal chamber of the sealing member and ambient air. In an invasive respiratory interface device, such as a laryngeal mask airway, the aperture may provide fluid communication between the internal chamber of the sealing member and a source of gas for inflating the sealing member.

According to a further aspect of the invention, there is provided a method of manufacturing a respiratory interface device, the method comprising the steps of:

(a) providing one or more moulds having a first cavity, a first polymer injection port, a second cavity, a second polymer injection port and a gas inlet port opening into the second cavity;

(b) injecting a first polymer through the first polymer injection port into the first cavity of the mould to form a body portion of the respiratory interface device;

(c) injecting a polymer and a blowing agent through the second polymer injection port into the second cavity of the one or more moulds, and introducing gas through the gas inlet port into the second cavity of the one or more moulds, to form a sealing member of the respiratory interface device, the sealing member of the respiratory interface device comprising an internal chamber at least partially bounded by a resiliently deformable enclosing wall formed of the second polymer, the enclosing wall including a patient-contacting surface;

wherein the body portion and the sealing member of the respiratory interface device may be formed in any order, such that either the body portion or the sealing member is an earlier-formed portion and the other of the body portion and the sealing member is a later-formed portion, and the later-formed portion is brought into engagement with the earlier-formed portion, during injection moulding of the later-formed portion, in a manner that fixes the body portion and the sealing member of the respiratory interface device together.

The patient-contacting surface may have a form that is determined by the second cavity of the mould. The patient-contacting surface may provide an anatomical fit with a patient. The blowing agent may expand in the second cavity of the mould.

The internal chamber at least partially bounded by a resiliently deformable enclosing wall formed of the polymer may be formed in the sealing member in the second cavity of the mould. The second cavity of the mould may be only partially charged by the second polymer and the blowing agent. The blowing agent may be activated by the application of heat. The polymer may be mixed with the blowing agent prior to injection into the second cavity of the mould, and the gas may be introduced through the gas inlet port into the second cavity of the mould when it is at least partially charged by the mixed polymer and blowing agent.

The gas inlet port may project relative to a surrounding interior surface of the mould that defines either the first or second cavity, such that an aperture is formed in the body portion of the respiratory device and/or the enclosing wall of the sealing member of the respiratory interface device, and the aperture may be in fluid communication with the internal chamber of the sealing member of the respiratory interface device.

The body portion of the respiratory interface device formed by the method according to the invention may comprise a flow passageway. The sealing member may be for sealing against a surface of the patient's body, which may be an external or internal surface, in order to form an effective seal with an airway of the patient. The flow passageway may be defined by a mask body in a respiratory mask and an airway tube in an endotracheal tube or laryngeal mask airway, for example. The body portion of the respiratory interface device may also comprise a connector for connecting the flow passageway of the device to respiratory apparatus, such as a breathing tube and/or a supply of respiratory gases.

The body portion of the respiratory interface device will typically be the earlier-formed portion, and the sealing member of the respiratory interface device will typically be the later-formed portion. However, there may be advantages to the sealing member of the respiratory interface device being the earlier-formed portion, and the body portion of the respiratory interface device being the later-formed portion, in some embodiments.

The one or more moulds having a first cavity, a second cavity, and a gas inlet port opening into the second cavity, may be arranged to enable the earlier-formed portion of the respiratory interface device to be disposed adjacent to or within the cavity (either the first or second cavity) for forming the later-formed portion of the respiratory interface device, such that the later-formed portion is brought into engagement with the earlier-formed portion, during injection moulding of the later-formed portion, in a manner that fixes the body portion and the sealing member of the respiratory interface device together. The later-formed portion may be brought into contact with the earlier-formed portion, during injection moulding of the later-formed portion.

The fixing between the body portion and the sealing member may be by one or more of a chemical bond and a mechanical bond. The bond may be formed immediately following the injection moulding of the later-formed portion of the respiratory interface device, such that no further assembly steps are required to fix the body portion and the sealing member together.

The second polymer may contact a border region of the body portion of the respiratory interface device, eg the mask body or airway tube, which may include a peripheral edge. Where the second polymer contacts a single border region of the body portion of the respiratory interface device, the internal chamber may be bounded only by the enclosing wall defined by the second polymer.

The gas inlet port may project relative to a surrounding interior surface of the mould that defines either the first or second cavity, which may cause an aperture to be formed in either the body portion of the respiratory device, and/or the enclosing wall of the sealing member of the respiratory interface device.

The gas inlet port of the mould may project relative to a surrounding interior surface of the mould that defines the second cavity, into the second cavity.

In this embodiment, the earlier-formed portion may be formed in the first or second cavity of the mould in a first-shot configuration, and the mould may then be moved to a second-shot configuration such that the earlier-formed portion of the respiratory interface device is disposed adjacent to the other of the first or second cavities for forming the later-formed portion of the respiratory interface device, and the later-formed portion is brought into engagement with the earlier-formed portion, during injection moulding of the later-formed portion, in a manner that fixes the body portion and the sealing member of the respiratory interface device together. For example, in the second-shot configuration of the mould, a surface of the body portion of the respiratory interface device, such as a peripheral edge of the body portion and a border region of the surface of the body portion adjacent to the peripheral edge, may be exposed to the interior of the cavity for forming the later-formed portion of the respiratory interface device. It is noted that the first cavity may be defined by the mould in the first-shot configuration, and the second cavity may be defined by the mould in the second-shot configuration, but the first and second cavities are not necessarily defined by the mould simultaneously. The mould may therefore be provided in a single injection moulding machine, and the process is typically called two-shot moulding.

Alternatively, the one or moulds may comprise a first mould defining the first cavity and a second mould defining the second cavity. In this embodiment, following formation of the earlier-formed portion of the respiratory interface device in the first or second mould, the first or second mould may be opened and the earlier-formed portion may be transferred to the other of the first and second moulds, such that the earlier-formed portion of the respiratory interface device is disposed within the cavity for forming the later-formed portion of the respiratory interface device, and the later-formed portion is brought into engagement with the earlier-formed portion, during injection moulding of the later-formed portion, in a manner that fixes the body portion and the sealing member of the respiratory interface device together. The first and second moulds may therefore be provided in two separate injection moulding machines, and the process is typically called overmoulding.

The method of manufacturing a respiratory interface device may therefore be a two-shot moulding process or an overmoulding process, and in both of these processes the body portion of the respiratory interface device will typically be the earlier-formed portion, and the sealing member of the respiratory interface device will typically be the later-formed portion. These two embodiments are defined separately below.

The sealing member of the respiratory interface device may be fixed to the body portion of the respiratory interface device by a chemical or mechanical bond, eg of the form provided by either two-shot moulding or overmoulding. The bond between the body portion and the sealing member may be permanent.

The above methods of manufacture may use one or more mould tools that define one or more moulds provided with a first cavity and a second cavity, with each cavity being defined by interior walls of the mould.

The gas inlet port of the mould may project into the second cavity. The gas inlet port may project relative to a surrounding interior surface of the mould that defines the second cavity. Alternatively, the gas inlet port may project through the body portion of the respiratory mask into the second cavity, eg through an aperture formed during injection moulding in the first mould.

Each cavity may have a single polymer injection port, which may have an exit opening into the cavity through which the polymer enters the cavity. The exit opening of the polymer injection port may be aligned with a longitudinal axis of the second cavity, and hence a longitudinal axis of the respiratory interface device.

The longitudinal axis of the respiratory interface device may correspond to the longitudinal axis of a patient, when the respiratory interface device is fitted to the patient. For a respiratory mask, the polymer injection port may be disposed at the end of the second cavity that corresponds to the apex of the nose portion of the respiratory mask. The exit opening may be formed in a wall of the mould and may be co-planar with a surrounding interior surface of the mould that defines the cavity.

The first polymer may be injected into the first cavity in the form of a polymer melt, which is polymer liquid above its glass and/or crystallization temperatures. The second polymer and the blowing agent may be injected into the second cavity in the form of a mixed melt. However, the process of injection moulding will differ depending on whether the polymer is a thermoplastic or a thermosetting plastic. Furthermore, in Liquid Injection Moulding, the first polymer and the second polymer-blowing agent mix may be a liquid mixture, rather than a polymer melt, which is cured within the mould, eg by the application of heat.

The injection moulding step may involve an injection unit. The injection unit may be configured to heat the polymer until it is soft enough to flow, thereby forming a polymer melt, and the injection unit may be moved into engagement, and fluid communication, with the injection port of the cavity of the mould. The injection unit may then apply pressure to the polymer melt, and inject the polymer melt through the polymer injection port into the cavity of the mould. Where the polymer is a thermoplastic, the polymer melt within the cavity is cooled to solidify the polymer. Where the polymer is thermosetting, the polymer may be heated in the injection unit so that it is soft enough to flow, but at a temperature that does not initiate curing, and the polymer melt within the cavity may be heated to initiate curing of the polymer. Alternatively, in Liquid Injection Moulding, the polymer may be a liquid mixture, rather than a polymer melt, which may be at room temperature or below in the injection unit, and then cured within the mould, eg by the application of heat.

A first injection unit may be provided with a first polymer. The first polymer may be heated in the injection unit until it is soft enough to flow, thereby forming a first polymer melt, and the first injection unit may be moved into engagement, and fluid communication, with the injection port of the first cavity of the mould.

A second injection unit may be provided with a second polymer and a blowing agent. The second polymer may be heated in the second injection unit until it is soft enough to flow, thereby forming a second polymer melt. The second polymer melt and the blowing agent may be mixed in the second injection unit. The second injection unit may be moved into engagement, and fluid communication, with the injection port of the second cavity of the mould.

The first polymer is injected into the first cavity of the mould to form the body portion of the respiratory interface device, eg a mask body of a respiratory mask or an airway tube of a laryngeal mask airway or an endotracheal tube. The first polymer may be polypropylene, poly(styrene-butadiene-styrene) (SBS), polycarbonate, or other suitable material. The first polymer and the second polymer may be different.

The second polymer and the blowing agent are injected into the second cavity of the mould to form the sealing member of the respiratory interface device. The second polymer may have an elastic modulus that is lower than the corresponding elastic modulus of the first polymer. The second polymer may be a thermoplastic elastomer or a thermoset elastomer, such as liquid silicone rubber.

Where a two-shot moulding process is used, the polymer for the later-formed portion may be injected into the cavity of the mould before the polymer for the earlier-formed portion has completely solidified, following completion of injection of the polymer for the earlier-formed portion. Where an overmoulding process is used, the earlier-formed portion of the respiratory interface device may be substantially or completely solidified before being transferred to the cavity for forming the later-formed portion of the respiratory interface device.

Where the polymer is a thermoplastic, the polymer melt will be heated above ambient temperature before injection, such that the polymer melt is able to flow, and the polymer melt will retain an elevated temperature relative to ambient temperature during the injection step. The polymer melt will solidify once sufficiently cooled. By ambient temperature is meant typical room temperature, eg 15-25° C.

Where the polymer is thermosetting, the polymer may be heated in the injection unit so that it is soft enough to flow, but at a temperature that does not initiate curing. Alternatively, in Liquid Injection Moulding, the polymer may be a liquid mixture, rather than a polymer melt, which is cured within the mould, eg by the application of heat. The polymer may then be injected into the cavity of the mould. The injection of gas and the forming of the sealing member would be the same as that for thermoplastics. However, the polymer is not allowed to cool and solidify. Instead, the mould is heated, eg at temperatures from 180 to 200° C., in order to initiate curing.

The methods of manufacturing a respiratory interface device above may include any, or any combination of, the methods of manufacturing a sealing member for a respiratory interface device defined above.

According to a further aspect of the invention, there is provided a respiratory interface device manufactured by the method as defined above.

According to a further aspect of the invention, there is provided a respiratory interface device comprising a body portion and a sealing member, the body portion comprising a first polymer, and the sealing member comprising a second polymer, the sealing member being fixed to the body portion, and the sealing member comprising an internal chamber at least partially bounded by a resiliently deformable enclosing wall formed of the second polymer, the enclosing wall including a patient-contacting surface and having a plurality of gas pockets formed therein.

The sealing member may additionally comprise a blowing agent within the second polymer.

The respiratory interface device may be a non-invasive interface device, such as a face mask, eg a full-face mask or a nasal mask, or a tracheostomy mask. Alternatively, the respiratory interface device may be an invasive interface device, such as an endotracheal tube, or may be a supraglottic airway, such as a laryngeal mask airway.

The respiratory interface device may include an aperture in the enclosing wall of the sealing member and/or in a wall of the body portion of the respiratory interface device, such that the aperture is in fluid communication with the internal chamber of the sealing member of the respiratory interface device and ambient air may enter and exit the internal chamber during use.

Where the patient-contacting surface additionally provides an anatomical fit with a patient, in combination with an internal chamber at least partially bounded by the resiliently deformable enclosing wall and an aperture through which ambient air may enter and exit the internal chamber during use, this combination of features provides the sealing member with an effective seal with a patient by virtue of its anatomical fit, but also enables the sealing member to be urged against the patient, eg against the patient's face, in the event that the seal needs to be improved, by virtue of its internal chamber and aperture through which ambient air may enter and exit the internal chamber during use.

In particular, the internal chamber and the aperture through which ambient air may enter and exit the internal chamber during use provides the sealing member with greater deformability for a given thickness of the resiliently deformable enclosing wall, relative to inflatable sealing members of the prior art. Furthermore, relative to sealing members of the prior art that are not inflatable, the arrangement of this aspect of the invention reduces the risk that the sealing member will splay, creating a leak, when pressure is applied by a clinician.

The aperture may be normally open, or may be opened by the flow of air into and out of the internal chamber of the sealing member. The aperture may be devoid of any valve having a closed configuration. In some embodiments, the aperture may include a valve that regulates the flow of ambient air into and out of the internal chamber of the sealing member. The valve may be a two-way valve. Where the aperture is formed in a wall of a mask body of the respiratory interface device, and any underlying wall of the sealing member, there may be a reduced risk of the aperture being occluded, during use.

This feature may improve the compliance of the sealing member when urged against a surface of the patient, in use, and hence improve the seal achieved with that surface.

In this arrangement, the gas pressure within the internal chamber may be atmospheric, and the enclosing wall may nevertheless have a sufficient rigidity to retain its shape during handling, eg unless urged with sufficient pressure against a patient's face during use.

If the user urges the sealing member against the surface of the patient, eg by applying pressure on the respiratory device interface towards the surface of the patient, the sealing member and the internal chamber would be compressed, causing air to exit the internal chamber. However, the rigidity of the sealing member may be sufficient for the internal chamber not to fully collapse during compression, ie there would remain a separation between opposing internal surfaces of the enclosing wall, and the rigidity of the sealing member may be sufficient for the enclosing wall and the internal chamber to return to their original shapes once the pressure has been removed.

The respiratory interface device may be a non-invasive interface device, in which the sealing member may seal the flow passageway, eg the mask body, to the face of the patient, thereby forming an effective fluid connection between the flow passageway and the mouth and/or nose of the patient. Alternatively, the respiratory interface device may be an invasive interface device, in which the sealing member may seal the flow passageway to an interior surface of an airway of the patient, thereby forming an effective fluid connection between the flow passageway of the device, eg the airway tube, and the patient's airway.

The sealing member and/or the patient-contacting surface may be configured as a continuous loop, which may extend around an entrance to a flow passageway in the respiratory interface device.

The respiratory interface device may be a mask, in which the body portion of the respiratory interface device defines a mask body for accommodating either the nose, or the mouth and nose, and the sealing member is for engagement with a patient's face, and which may have the form of a sealing cushion. The body portion of the respiratory interface device may also comprise a connector for connecting the mask body of the device to respiratory apparatus, such as a breathing tube and/or a supply of respiratory gases. The connector may be disposed at the other end of the flow passageway defined by the mask body relative to the end at which the sealing member is disposed.

The respiratory interface device may be an endotracheal tube or a supraglottic airway, such as a laryngeal mask airway, in which the body portion of the respiratory interface device defines an airway tube, and the sealing member is for engagement with a patient's larynx or trachea, which may have the form of a sealing cuff. The body portion of the respiratory interface device may also comprise a connector for connecting the airway tube of the device to respiratory apparatus, such as a breathing tube and/or a supply of respiratory gases. The connector may be disposed at the other end of the flow passageway defined by the airway tube relative to the end at which the sealing member is disposed.

According to a further aspect of the invention, there is a breathing circuit comprising a supply of respiratory gases, a respiratory interface device as defined above, and a breathing tube extending between the supply of respiratory gases and the patient interface device.

Practicable embodiments of the invention will now be described, by way of example only, with reference to the accompanying drawings, of which:

The method according to an embodiment of the invention illustrated in FIGS. 1-6 is a two-shot injection moulding method for manufacture of a respiratory mask.

The injection moulding process typically involves apparatus comprising injection units that each include an outlet nozzle, a tool that defines the mould, and a clamp unit. The clamp unit is arranged to move a component of the mould tool between a closed configuration, in which the polymer melt may be injected into the cavities of the mould, and an open configuration, in which the formed article may be removed from the mould tool.

The mould tool defines a mould that is provided with a first cavity and a second cavity, with the first cavity having a polymer injection port for introducing a polymer melt into that cavity and the second cavity having a polymer injection port for introducing a polymer melt and a blowing agent into that cavity, each cavity being defined by interior walls of the mould.

A first injection unit for the first shot of the two-shot injection moulding method is provided with a first polymer melt which, in this embodiment, is polypropylene (PP), a thermoplastic. The first polymer melt is heated in the injection unit until it is soft enough to flow, and the outlet nozzle of the injection unit is moved into engagement, and fluid communication, with the injection port of the first cavity of the mould.

In addition, a second injection unit for the second shot of the two-shot injection moulding method is provided with a mixture of a second polymer melt and a blowing agent. In this embodiment, the second polymer melt is a thermoplastic elastomer (TPE), and the blowing agent is a plurality of microspheres, provided in masterbatch form. The blowing agent is added to the second polymer melt using a volumetric dosing unit to ensure an even distribution throughout the second polymer melt. The second polymer melt and the blowing agent are heated in the second injection unit until soft enough to flow, and the outlet nozzle of the second injection unit is moved into engagement, and fluid communication, with the injection port of the second cavity of the mould.

In the first shot of the method according to the first embodiment of the invention, the mould is moved to its first-shot configuration. The first injection unit then applies pressure to the first polymer melt, eg using a piston and cylinder arrangement (which may also be known in the field as a screw and barrel arrangement), and injects the first polymer melt through the outlet nozzle and through the polymer injection port into the first cavity of the mould. The polymer melt within the first cavity is then allowed to commence cooling, while the pressure applied to the polymer melt is maintained, until the polymer melt is partially solidified.

Figure 1:
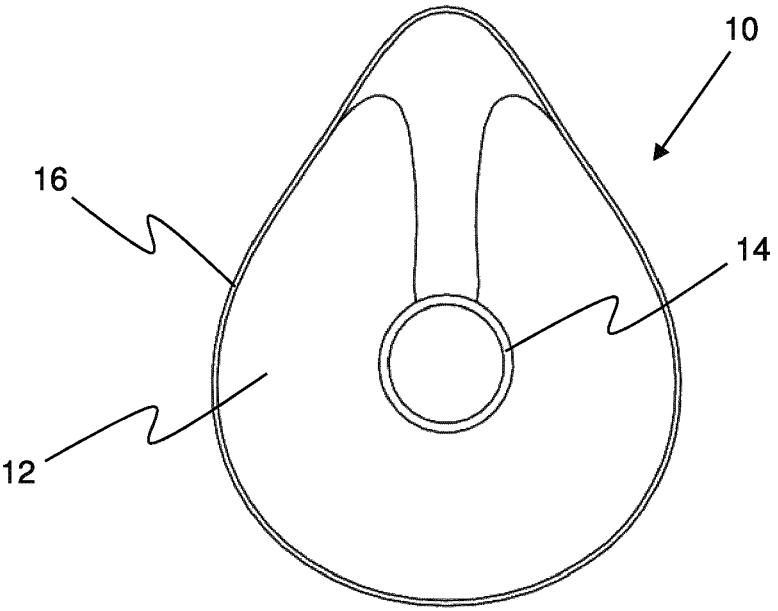
FIG. 1 is a rear view of a mask body formed in a first shot of a two-shot moulding method according to a first embodiment of the invention.

The polymer melt injected into the first cavity takes the form of a mask body 10. This mask body is shown in FIG. 1, with the mould not shown for clarity.

The mask body 10 comprises a peripheral edge 16, and a tapered wall 12 that extends forwardly and inwardly from the peripheral edge 16 to a tubular connector 14. The tubular connector 14 is a conventional male or female cylindrical connector, eg 22 mm diameter, for connection to a respiratory circuit. The tapered wall 12 is generally dome-shaped, with a mouth portion having a generally annular cross-section, in a plane that corresponds to the plane of a patient's face, in use, ie the frontal plane, and a narrowed nose portion that is generally triangular in shape, with a rounded apex for engagement with the bridge of the nose of the patient. In the mask body shown in FIG. 1, the nose portion of the tapered wall 12 also includes a narrowed portion along the longitudinal axis of the mask body, extending from the tubular connector 14 towards the rounded apex of the nose portion of the tapered wall 12. This narrowed portion of the tapered wall 12 defines side surfaces that may be gripped by a user, eg in a pinching action.

Once the mask body 10 has been formed, in a solidified or partially solidified state, in the first shot of the two-shot injection moulding method, the mould is then moved into the second-shot configuration, such that the second cavity of the mould is in fluid communication with the peripheral edge 16 of the mask body 10 and a border region of the surface of the mask body 10 adjacent to the peripheral edge 16.

In a second shot of the method according to the first embodiment of the invention, whilst the mask body 10 remains in a solidified or partially solidified state, the second injection unit applies pressure to the polymer melt-blowing agent mix, eg using a piston and cylinder arrangement, and injects the second polymer melt-blowing agent mix through the outlet nozzle and through the polymer injection port into the second cavity of the mould.

Figure 2:
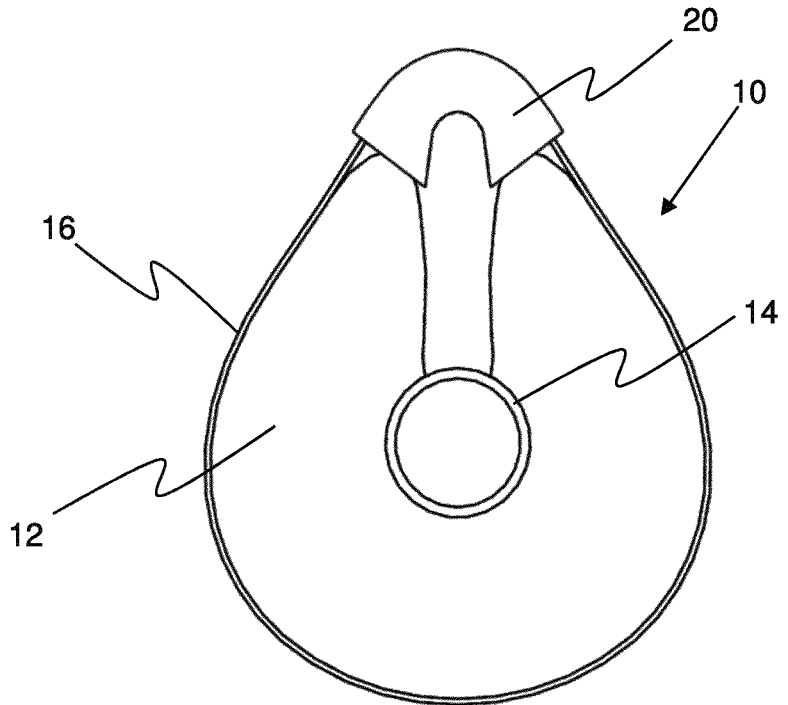
FIG. 2 is a schematic representation of a first stage of a second shot of the two-shot moulding method according to a first embodiment of the invention, in which a mixture of a polymer melt and a blowing agent of a second shot is being introduced.
Figure 3:
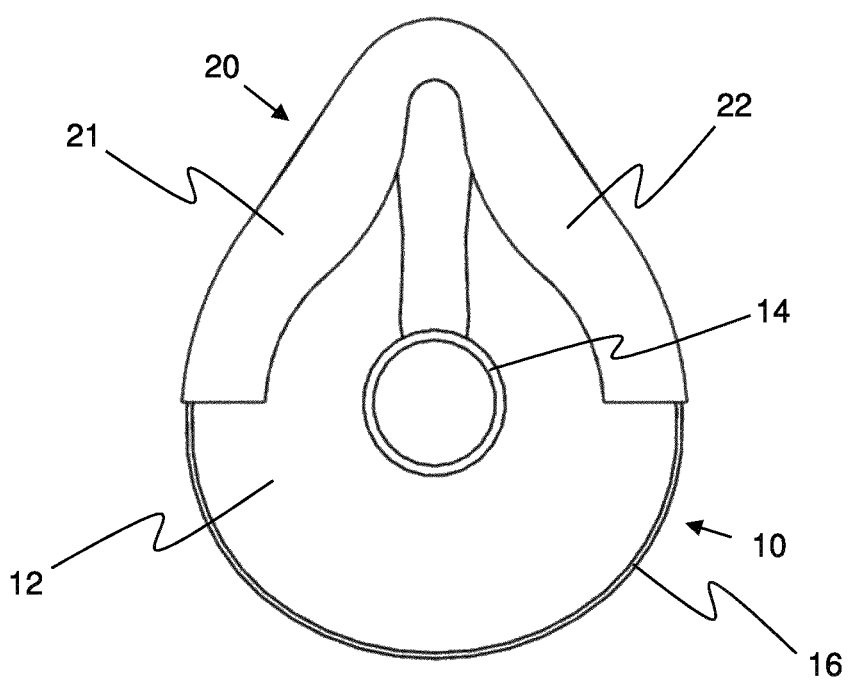
FIG. 3 is a schematic representation of a second stage of the second shot of the two-shot moulding method according to a first embodiment of the invention, in which the mixture of the polymer melt and the blowing agent of the second shot has been fully introduced.

FIG. 2 shows the second polymer melt-blowing agent mix 20 partially introduced into the second cavity, and FIG. 3 shows the second polymer melt-blowing agent mix 20 fully introduced into the second cavity.

The microspheres comprise a hydrocarbon core contained within a thermoplastic shell. Upon entering the second cavity, which is heated, the hydrocarbon core expands, and the thermoplastic shell gets gradually thinner, but maintains the shape of the microsphere so that the hydrocarbon is maintained therein. As the hydrocarbon core starts to expand, the volume of the second polymer melt-blowing agent mix 20 is increased, and hence, the volume of the cavity that is taken up by the second polymer melt-blowing agent mix 20 after injection into the cavity of the mould is greater than if the polymer were to be injected alone.

The second polymer melt-blowing agent mix 20 only partially charges the second cavity, as shown in FIG. 3, and hence the volume of the second polymer melt-blowing agent mix 20 is less than the volume of the second cavity. Since the polymer injection port 28 for the second cavity is disposed at the apex of the nose portion of the mask body 10 (see FIG. 6), and the second cavity extends in both directions from the polymer injection port 28 around the peripheral edge 16 of the mask body 10, the second polymer melt-blowing agent mix 20 flows along the second cavity in two branches 21, 22 from the polymer injection port 28, and extends substantially the same distance into the second cavity in each branch 21, 22.

Figures 5, 6:
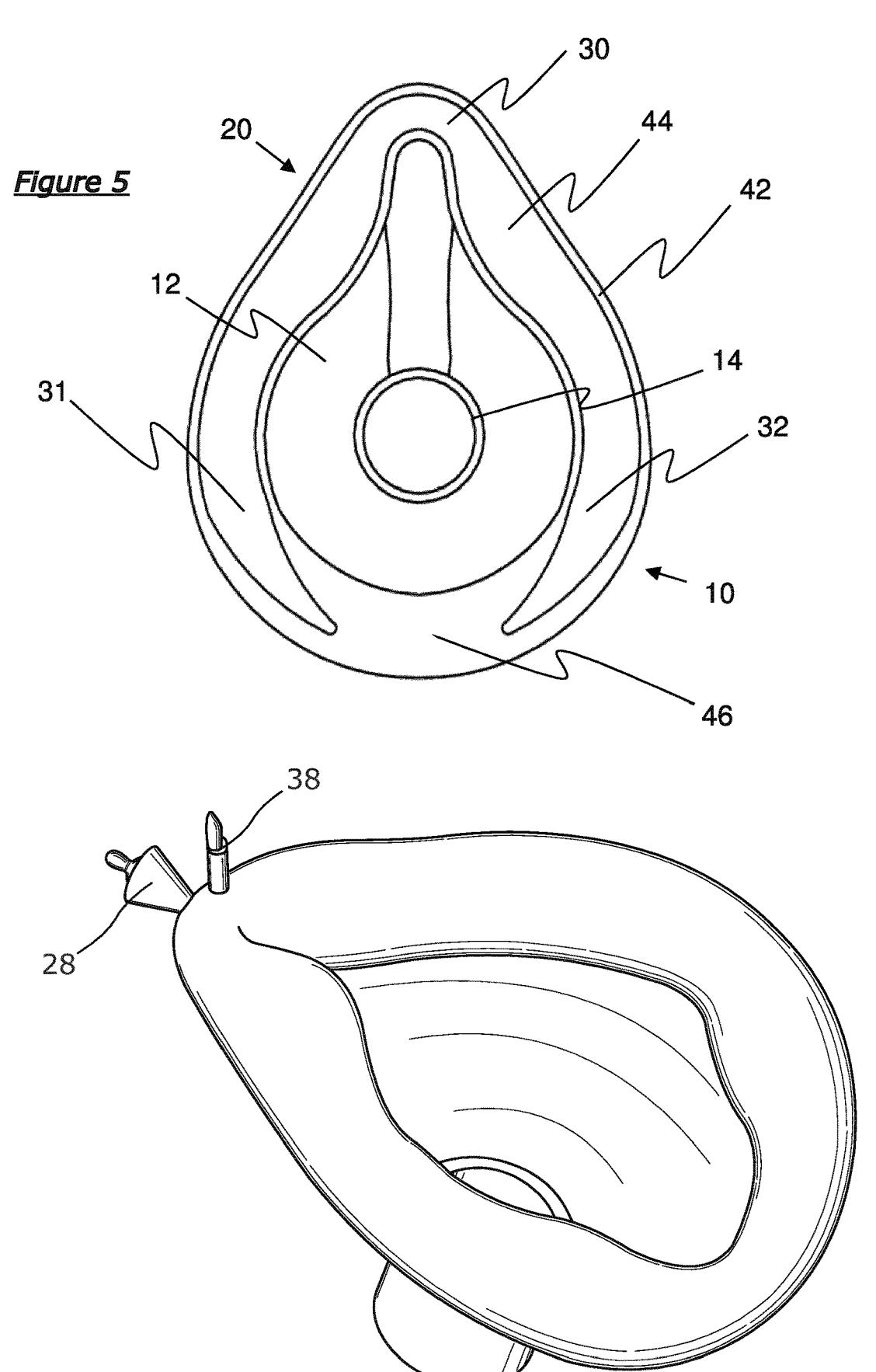
FIG. 5 is a schematic representation of a fourth stage of the second shot of the two-shot moulding method according to a first embodiment of the invention, in which the gas is fully introduced into the mixture of the polymer melt and the blowing agent of the second shot.
FIG. 6 is a respiratory mask formed by the two-shot moulding method according to a first embodiment of the invention, in which the polymer and gas inlets for the second shot are shown.

Once the second polymer melt-blowing agent mix 20 has been fully introduced into the second cavity, and partially charged the second cavity, nitrogen gas 30 is introduced into the second polymer melt-blowing agent mix 20 in the second cavity through a gas inlet port 38 (see FIG. 6). The gas inlet port 38 is situated adjacent to, and orientated perpendicularly to, the polymer injection port 28 for the second cavity. The gas inlet port 38 extends from a wall of the second cavity into a central region of the second cavity, such that the gas forms a bubble within the second polymer melt 20 in the second cavity.

Since the gas inlet port 38 is also disposed at the apex of the nose portion of the mask body 10, and the second cavity extends in both directions from the gas inlet port 38 around the peripheral edge 16 of the mask body 10, the bubble of gas 30 flows along a central axis of the second polymer melt 20 in the second cavity in two branches 31, 32 from the gas inlet port 38.

Figure 4:
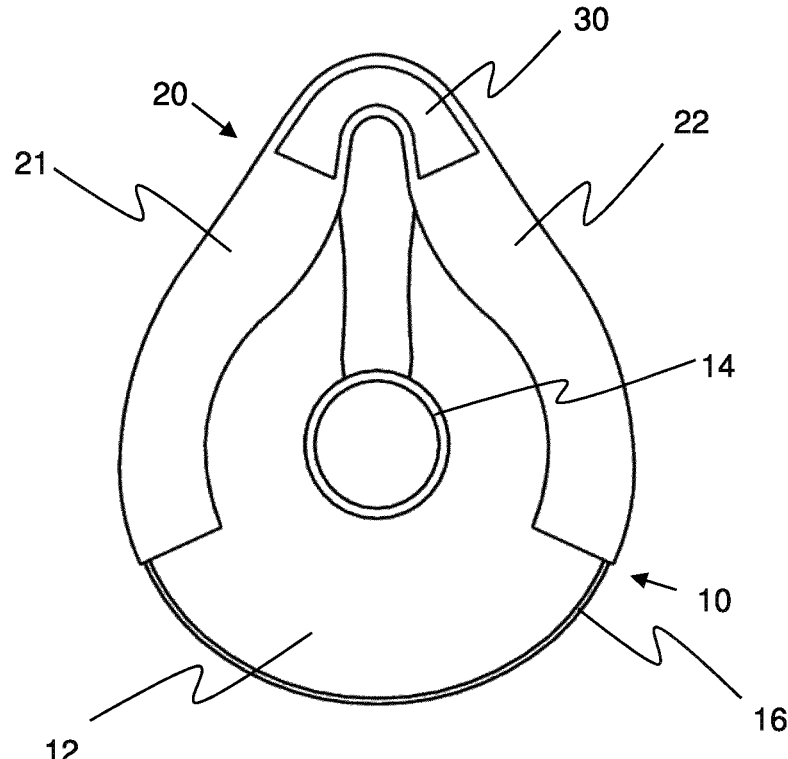
FIG. 4 is a schematic representation of a third stage of the second shot of the two-shot moulding method according to a first embodiment of the invention, in which a gas is partially introduced into the mixture of the polymer melt and the blowing agent of the second shot.

FIG. 4 shows the gas 30 partially introduced into the second polymer melt-blowing agent mix 20 of the second cavity, and FIG. 5 shows the gas fully introduced into the second polymer melt-blowing agent mix 20 of the second cavity.

As shown in FIGS. 4 and 5, the introduction of gas 30 moves the second polymer melt-blowing agent mix 20 even further along the second cavity, towards the chin region of the mask body 10, until the two branches 21, 22 of the second polymer melt-blowing agent mix 20 meet, mix and join in the chin region of the mask body 10. In this embodiment, the gas 30 introduced into the second polymer melt-blowing agent mix 20 in the second cavity is sufficient to form a thin-walled sealing cushion 42 from the second polymer melt-blowing agent mix 20, with a gas-charged internal chamber 44. However, the gas 30 introduced into the second polymer melt-blowing agent mix 20 in the second cavity remains in two branches 31, 32, and does not meet at the chin region of the mask body 10. Instead, the two branches 31, 32 of the gas-charged internal chamber 44 each terminate with a tapered end portion, with each tapered end portion being disposed to each side of a solid portion of the second polymer melt-blowing agent mix, ie a portion of the second polymer melt-blowing agent mix that does not contain a gas-charged interior, that forms a chin region 46 of the sealing cushion 42.

Once the sealing cushion 42 of the respiratory mask has been formed, the mask body 10 and the sealing cushion 42 are allowed to cool and completely solidify, whilst the pressure applied to the polymer melt-blowing agent mix by the gas 30 is maintained. The second polymer-blowing agent mix will bond to the border region and the peripheral edge of the mask body 10, such that the mask body 10 and the sealing cushion 42 of the respiratory mask are bonded together. There is therefore no need for additional assembly steps, such as gluing, to fix the mask body 10 and the sealing cushion 42 together.

The second cavity of the mould is shaped to provide the sealing cushion 42 of the respiratory mask with an anatomical shape, which is configured to correspond to the contours of a patient's face about their nose and mouth.

The sealing cushion 42 of the respiratory mask comprises a thin enclosing wall surrounding a gas-charged internal chamber 44. Furthermore, since the gas inlet port 38 extends from a wall of the second cavity into a central region of the second cavity, the wall of the sealing cushion 42 of the respiratory mask forms around the gas inlet port 38, which provides an aperture in the wall of the sealing cushion 42 of the respiratory mask when the respiratory mask is removed from the mould. This aperture in the wall of the sealing cushion 42 of the respiratory mask provides fluid communication between the gas-charged internal chamber 44 of the sealing cushion 42 of the respiratory mask and ambient air.

Figure 7:
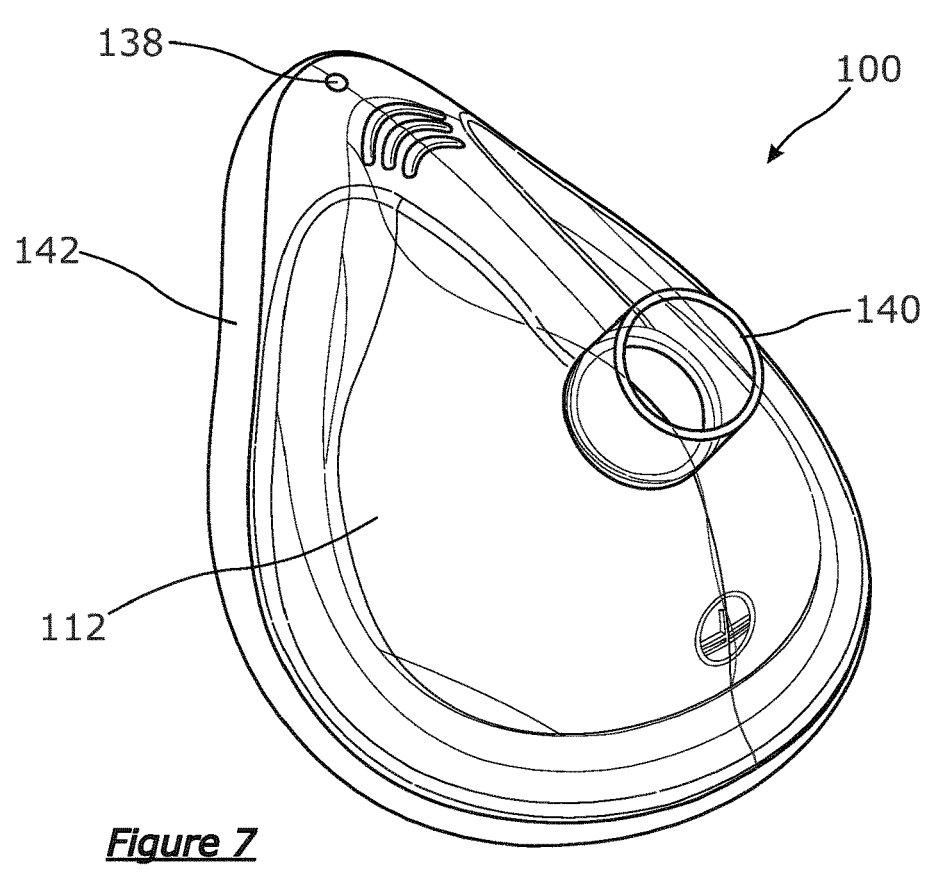
FIG. 7 is a first perspective view of a respiratory mask formed by two-shot moulding method according to a second embodiment of the invention.
Figure 8:
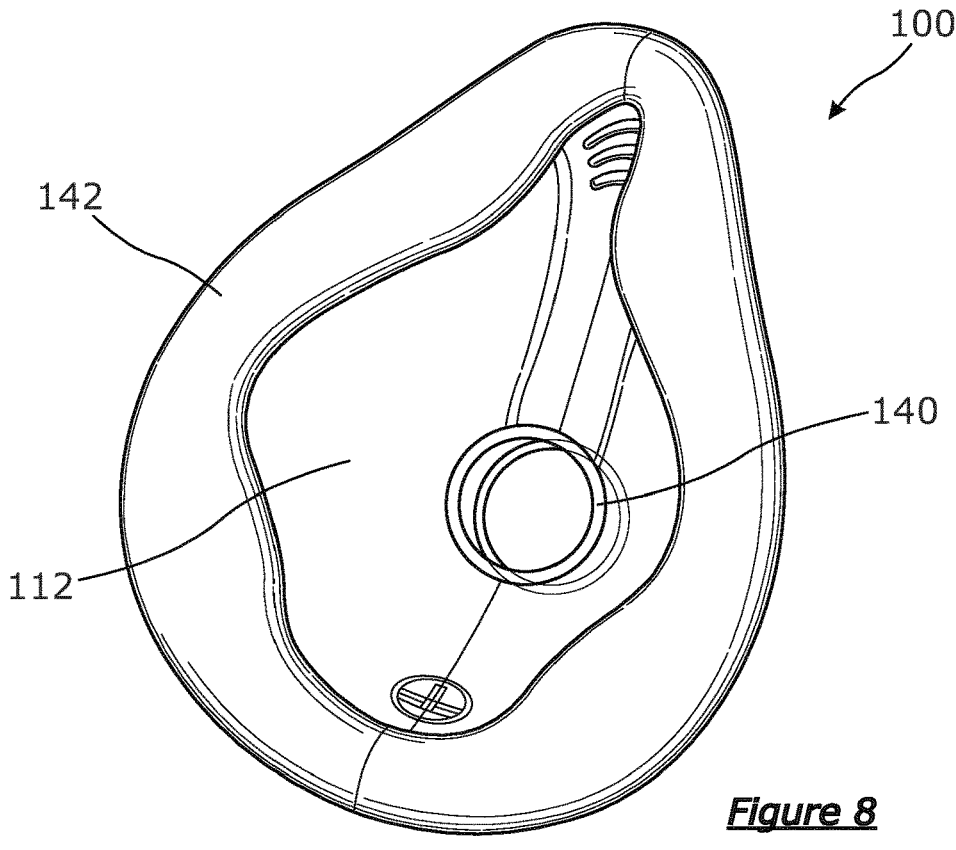
FIG. 8 is a second perspective view of the respiratory mask formed by the two-shot moulding method according to the second embodiment of the invention.

FIGS. 7 and 8 show a respiratory mask 100 that has been formed by a two-shot moulding method according to a second embodiment of the invention. This respiratory mask 100 is identical to those respiratory masks formed by the first embodiment of the method according to the invention, as described above, save for the location of the aperture 138 formed by the gas inlet port 38.

In the respiratory mask 100 formed by the second embodiment of the method according to the invention, the aperture 138 formed by the gas inlet port is located in the mask body 112 and an underlying wall of the sealing cushion 142, rather than in the deformable wall of sealing cushion 142 that extends from the mask body 112. This location of the aperture 138 is achieved by providing a mould in which the gas inlet port 38 extends from a wall of the first cavity of the mould and into a central region of the second cavity, in a second-shot configuration of the mould. In this arrangement, when the first polymer is injected into the first cavity of the mould to form the mask body 112 the mask body 112 forms around the gas inlet port 38. In a second-shot configuration of the mould, the gas inlet port 38 extends through the mask body 112 in the first cavity and projects into the second cavity. In this arrangement, when the second polymer-blowing agent mix is injected into the second cavity of the mould to form the sealing cushion 142, a wall of the sealing cushion 142 that underlies an adjacent wall of the mask body 112 forms around the gas inlet port 38. An aperture 138 is therefore formed in the mask body 112, and the underlying wall of the sealing cushion 142, of the respiratory mask 100 when the respiratory mask 100 is removed from the mould. This aperture 138 provides fluid communication between the gas-charged internal chamber of the sealing cushion 42 of the respiratory mask 100 and ambient air.

In a third embodiment of a method according to the invention, an overmoulding process is used. This differs from the first and second embodiments, which are two-shot moulding processes, in that the mask body formed of the first polymer (the substrate) is transferred to a second cavity in a second mould, typically once substantially or completely solidified, before the second polymer-blowing agent mix is injection moulded into the second cavity, and hence "overmoulds" the mask body. In this embodiment, the sealing member formed by the second polymer-blowing agent mix is fixed to the mask body formed by the first polymer by one or more of a chemical bond and a mechanical bond.

Furthermore, any of the first, second and third embodiments may also be used with a thermosetting polymer, eg for the sealing member. For example, liquid silicone rubber (LSR) may be the second polymer for forming the sealing member. However, where a thermosetting polymer is used, the injection moulding step and the associated apparatus will differ to these described above, as thermosetting polymers typically require heat to initiate curing in order to harden. For liquid silicone rubber, a liquid injection moulding (LIM) process is typically used.

The materials commonly used in the LIM process are silicones and acrylics. Utilising a pump, the LIM process brings together a base-forming plastic, which can be strengthened with additives and fibres, and a catalyst. Each will be pumped in a 1:1 ratio into a static mixer, which triggers the mixing reaction, to form liquid silicone rubber (LSR), for example. The outlet nozzle of the injection unit is moved into engagement, and fluid communication, with the injection port of the cavity of the mould. The liquid mixture is then injected into the cavity of the mould along with a blowing agent.

Described below are examples of respiratory masks formed by the applicant during testing, using the above-described methods.

EXAMPLE 1

In a first example, a polymer-blowing agent mix consisting of 95% thermoplastic elastomer and 5% blowing agent in the form of microsphere masterbatches produced by KCD GmbH (Otto-Schott-Straße 5, 99427 Weimar, Deutschland) produced a sealing member having a substantially uniform enclosing wall and internal chamber, with the enclosing wall having a wall thickness that varied between 2 mm and 3 mm.

EXAMPLE 2

In a second example, a polymer-blowing agent mix consisting of 90% thermoplastic elastomer and 10% blowing agent in the form of microsphere masterbatches produced by Expancel (Nouryon, Pulp and Performance Chemicals AB, Box 13000, SE-850 13 Sundsvall, Sweden) produced a sealing member having a substantially uniform enclosing wall and internal chamber, with the enclosing wall having a wall thickness that varied between 1.5 mm and 2 mm.

The invention claimed is:

1. A method of manufacturing a sealing member, the method comprising the steps of:

(a) providing a mould having a cavity, a polymer injection port and a gas inlet port;

(b) injecting a polymer and a blowing agent through the polymer injection port into the cavity of the mould; and (c) introducing gas through the gas inlet port into the cavity of the mould, to form the sealing member, wherein the sealing member comprises an internal chamber at least partially bounded by a resiliently deformable enclosing wall formed of the polymer, the enclosing wall including a patient-contacting surface, the patient-contacting surface having a form that is determined by the cavity of the mould.

2. A method of manufacturing a sealing member according to claim 1, wherein the dimensions of the patient-contacting surface are determined by the cavity of the mould, and/or wherein the volume of the sealing member is determined by the cavity of the mould.

3. A method of manufacturing a sealing member according to claim 1, wherein the final form of the material formed from the polymer and the blowing agent is determined by the cavity of the mould, and/or wherein the sealing member fully sets or fully solidifies in the cavity of the mould.

4. A method of manufacturing a sealing member according to claim 1, wherein the shape and/or dimensions of the patient-contacting surface matches, or corresponds to, the shape and/or dimensions of the cavity of the mould, and/or wherein the volume of the sealing member matches, or corresponds to, the volume of the cavity of the mould.

5. A method of manufacturing a sealing member according to claim 1, wherein the sealing member adopts its final form in the cavity of the mould.

6. A method of manufacturing a sealing member according to claim 1, wherein the sealing member cools in the cavity of the mould before opening of the mould to a temperature low enough for the sealing member to undergo no substantial change in inherent shape or dimensions upon opening of the cavity or removal of the sealing member from the cavity of the mould.

7. A method of manufacturing a sealing member according to claim 1, wherein the blowing agent is a physical blowing agent that provides gas expansion by a physical process.

8. A method of manufacturing a sealing member according to claim 7, wherein the blowing agent is caused to expand by one of, or a combination of, the application of heat and a reduction in pressure on injection of the polymer and blowing agent mix into the cavity of the mould.

9. A method of manufacturing a sealing member according to claim 1, wherein the blowing agent expands in the cavity of the mould before opening of the mould.

10. A method of manufacturing a sealing member according to claim 1, wherein the patient contacting-surface provides an anatomical fit with a patient.

11. A method of manufacturing a sealing member according to claim 10, wherein the patient-contacting surface has a leading portion, which is a portion that contacts a surface of the patient before any deformation of the sealing member, that is anatomically shaped at least in a direction of engagement of the sealing member with the surface of the patient, such that a position of the leading portion of the patient-contacting surface varies in this direction, at different positions along the patient-contacting surface.

12. A sealing member manufactured by the method according to claim 1.

13. A respiratory interface device comprising a sealing member manufactured by the method according to claim 1.

14. A method of manufacturing a sealing member according to claim 1, wherein the gas is first introduced through the gas inlet port into the cavity of the mould after the cavity of the mould is at least partially charged by a mixture of the polymer and blowing agent, and/or wherein the polymer and the blowing agent are injected through the polymer injection port into the cavity of the mould such that the cavity of the mould is only partially charged.

15. A sealing member comprising an enclosed internal chamber at least partially bounded by a resiliently deformable enclosing wall, the enclosing wall including an external surface, the enclosing wall having a plurality of gas pockets formed therein, the sealing member having the form of a loop, and the internal chamber of the sealing member being continuous and extending around at least a majority of the loop.

16. A sealing member according to claim 15, wherein the enclosed internal chamber has a central longitudinal axis that follows a curved path, and the curved path extends around at least the majority of the loop.

17. A sealing member according to claim 15, wherein the gas pockets have an appearance akin to bubbles, a cellular structure, or a matrix of holes.

18. A sealing member according to claim 15, wherein a majority of gas pockets have a diameter in the range of 50-500 μm.

19. A respiratory interface device comprising a sealing member as claimed in claim 15.

20. A sealing member according to claim 15, wherein an aperture is formed in the enclosing wall of the sealing member, and the aperture is in fluid communication with the internal chamber of the sealing member, such that ambient air may enter and exit the internal chamber during use.

21. A respiratory interface device comprising a body portion and a sealing member, the body portion comprising a first polymer, and the sealing member comprising a second polymer, the sealing member being fixed to the body portion, wherein the sealing member comprises an enclosed internal chamber at least partially bounded by a resiliently deformable enclosing wall formed of the second polymer, the enclosing wall including a patient-contacting surface and having a plurality of gas pockets formed therein, the sealing member having the form of a loop, and the internal chamber of the sealing member being continuous and extending around at least a majority of the loop.

22. A respiratory interface device according to claim 21, wherein an aperture is formed in the enclosing wall of the sealing member, and the aperture is in fluid communication with the internal chamber of the sealing member, such that ambient air may enter and exit the internal chamber during use.

* * * * *